(12) United States Patent
Zeller et al.

(10) Patent No.: US 6,353,141 B1
(45) Date of Patent: Mar. 5, 2002

(54) FUNCTIONALIZED CYCLOPENTENE-DERIVED OLIGOMER MIXTURES, THEIR PREPARATION AND THEIR USE

(75) Inventors: Edgar Zeller, Mannheim; Gerhard Schulz, Ludwigshafen; Bernhard Geissler, Kirchheim; Michael Röper, Wachenheim; Guido Voit, Schriesheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/331,419

(22) PCT Filed: Dec. 23, 1997

(86) PCT No.: PCT/EP97/07260

§ 371 Date: Jun. 21, 1999

§ 102(e) Date: Jun. 21, 1999

(87) PCT Pub. No.: WO98/28252

PCT Pub. Date: Jul. 2, 1998

(30) Foreign Application Priority Data

Dec. 23, 1996 (DE) .......................................... 196 54 167

(51) Int. Cl.[7] .......................... C07C 45/00; C07C 35/21
(52) U.S. Cl. ...................... 568/444; 568/667; 568/816; 560/114
(58) Field of Search ................................ 568/444, 667, 568/816; 560/114

(56) References Cited

U.S. PATENT DOCUMENTS 3,527,828 A * 9/1970 Mango et al. ............... 260/677
4,584,411 A * 4/1986 Johnson ...................... 568/451
4,808,756 A * 2/1989 Tokitoh et al. .............. 568/454

OTHER PUBLICATIONS

"Scattering to Structural Foams", Encyclopedia of Polymer Science and Engineering, pp. 665–668, vol. 15, 1992, John Wiley & Sons.*

"Peroxy Compounds to Polyesters", Encyclopedia of Polymer Science and Engineering, pp. 287–288, vol. 11, 1992, John Wiley & Sons.*

"Liquid Crystalline Polymers to Mining Applications", Encyclopedia of Polymer Science and Engineering, pp. 634–636, vol. 9, 1992, John Wiley & Sons.*

* cited by examiner

Primary Examiner—Ralph Gitomer
Assistant Examiner—Devesh Khare
(74) Attorney, Agent, or Firm—Keil & Weinkauf

(57) ABSTRACT

Functionalized cyclopentene-derived oligomer mixtures are prepared by reacting oligomer mixtures which contain ethyleneic double bonds in one or more reaction steps starting from cyclopentene-derived oligomer mixtures of the formula I $$R^1R^2C=[=CH-(CH_2)_3-CH=]_n=CR^3R^4 \qquad (I)$$

where n is an integer from 1 to 15, and $R^1$, $R^2$, $R^3$ and $R^4$ are, independently of one another, hydrogen or alkyl, and are used as described.

17 Claims, No Drawings

FUNCTIONALIZED CYCLOPENTENE-DERIVED OLIGOMER MIXTURES, THEIR PREPARATION AND THEIR USE

This application is a 371 of PCT/EP97/07260 filed Dec. 23, 1997.

Functionalized cyclopentene-derived oligomer mixtures, their preparation and their use The present invention relates to functionalized cyclopentene-derived oligomer mixtures, processes for their preparation by hydroformylation and, where appropriate, further reaction of corresponding oligomer mixtures which contain ethylenic double bonds, and their use.

The processing of petroleum by steam cracking results inter alia in a hydrocarbon mixture which is called the $C_5$ cut and has a high total olefin content of, for example, about 50%, of which about 15% is made up of cyclopentene and the remainder of acyclic monoolefins, especially n-pentene (about 15% by weight) and other isomeric pentenes (about 20% by weight). This mixture can, if required, before further processing be subjected to partial catalytic hydrogenation so that dienes are essentially no longer present then. To isolate the cyclopentane which comprises about 8% of the $C_5$ cut and which is employed, for example, as propellent as substitute for the CFCs and HFCs which are of concern with regard to damage to the atmosphere, and where appropriate to isolate the other saturated acyclic pentanes, it is necessary in the prior art to subject the $C_5$ cut to work up by distillation. This is technically a very complicated process when acyclic and cyclic $C_5$ olefins, in particular cyclopentene, are simultaneously present. There is thus a need for a process for removing cyclopentene and, where appropriate, other monoolefins from the $C_5$ cut other than by distillation, where possible with simultaneous production of a new product of value.

It is possible for this purpose to subject the $C_5$ cut to a metathesis reaction in the presence of a transition metal catalyst, resulting in new cyclopentene-derived oligomer mixtures with ethylenic double bonds.

A known process for the functionalization of polymers with ethylenic double bonds is hydroformylation. Thus, for example, M. P. McGrath et al., describe, in J. Appl. Polym. Sci. 56, (1995) 533 et seq., the hydroformylation of EPDM polymers and polybutadienes with $HRhCO(PPh_3)_3$ or $Rh(CO)_2acac$ (acac=acetylacetonato) as hydroformylation catalysts in toluene. Reviews on the hydroformylation of polymers with olefinic double bonds, such as polyisoprene or styrene/butadiene copolymers, are given by N. T. McManus et al. in J. Macromol. Sci., Rev. Macromol. Chem. Phys. C35(2) (1995) 239–285.

Aldehyde-functionalized polymers of this type in turn permit reactions to be carried out on the polymer, ie. conversion into or attachment of new functionalities which confer new properties on the polymer.

C. Azuma et al. describe in J. Polym. Sci., Polymer Chemistry Edition, 18, (1980) 781 et seq. the hydroformylation of a polypentenamer with a number average molecular weight of 94,000 in the presence of an $HRhCO(PPh_3)_3$ catalyst, and the subsequent conversion into the oxo alcohols with various reducing agents such as sodium borohydride. The amounts of catalyst needed for this hydroformylation are extremely high at about 5000 ppm. Hydroformylation of the polymer is possible only to a maximum aldehyde content of 30 mol %, otherwise insoluble products result. It is likewise necessary for the hydroformylated polymers to be reacted further immediately, without isolation, otherwise crosslinking occurs, likewise resulting in completely insoluble products.

K. Weissermel, H. J. Arpe, Industrielle Organische Chemie, 4th edition, 1994, VCH Weinheim, pages 137 et seq. describe the hydroformylation (oxo synthesis) of olefins by reaction with carbon monoxide and hydrogen in the presence of a catalyst and generally at elevated temperatures under elevated pressures. The oxo aldehydes obtained therefrom have virtually no importance as final products but are important reactive intermediates for preparing oxo alcohols, oxo carboxylic acids and aldol condensates. It is furthermore possible for oxo aldehydes to be converted by reductive amination with ammonia or a primary or secondary amine in the presence of a reducing agent into the corresponding amines.

The oxo alcohols can in principle be prepared together with the hydroformylation, usually at elevated temperature, in a one-stage synthesis because the hydroformylation catalysts are generally also suitable for further hydrogenation of the oxo aldehydes. However, the oxo aldehydes are usually first isolated and then subjected to a catalytic hydrogenation on a specific hydrogenation catalyst selected from metals in group VIII or Ib, eg. a Cu or Ni catalyst.

To prepare oxo carboxylic acids, the oxo aldehydes can be oxidized with mild oxidizing agents, in the simplest case with air or with $H_2O_2$ in the presence of acids. The oxidation with air can take place either catalytically in the presence of metal salts or else in the absence of catalysts at up to about 100° C. under pressures up to about 7 bar.

Houben-Weyl, Methoden der organischen Chemie, Volume XI/1, 1957, pages 602 et seq., describes the reduction of condensates of ammonia or amines and carbonyl compounds, and the reductive amination of carbonyl compounds, the latter, eg. an aldehyde, being reacted with ammonia or a primary or secondary amine in the presence of a reducing agent without isolation of an intermediate. The reducing agent generally used is hydrogen in the presence of a hydrogenation catalyst, but it is also possible to use other reducing agents, such as formic acid and its derivatives. None of the abovementioned publications refers to a process for functionalizing oligomers derived from cyclopentene and obtainable by a metathesis reaction of the $C_5$ cut from petroleum processing.

It is an object of the present invention to provide a process for further processing of the new oligomer mixtures produced by a metathesis reaction on the $C_5$ cut.

We have found that this object is achieved by a process for preparing functionalized cyclopentene-derived oligomer mixtures, where the cyclopentene-derived oligomer mixtures which contain ethylenic double bonds are subjected to a hydroformylation and, where appropriate, further functionalizations.

The invention thus relates to a process for preparing functionalized cyclopentene-derived oligomer mixtures by a single stage or multistage functionalization of at least some of the ethylenic double bonds present in an oligomer mixture of the formula I

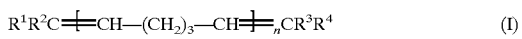  (I)

where n is an integer from 1 to 15, and $R^1$, $R^2$, $R^3$ and $R^4$ are, independently of one another, hydrogen or alkyl.

The value of n in the formula I is the number of cyclopentene units introduced by a ring-opening metathesis reaction into the cyclopentene-derived oligomer mixtures. The oligomer mixtures of the formula I preferably used for the process according to the invention are those where the value of n is >1 in a proportion which is as large as possible, eg. at least 40% by weight (determined by integration of areas in the gas chromatograms). The value of n and thus the extent of the ring-opening metathesis can be influenced by the activity of the metathesis catalyst used and the ratio of acyclic to cyclic olefins.

The radicals $R^1$, $R^2$, $R^3$ and $R^4$ in the formula I are, independently of one another, hydrogen or alkyl, where the term "alkyl" embraces straight-chain and branched alkyl groups.

These are preferably straight-chain or branched $C_1$–$C_{15}$-alkyl, preferably $C_1$–$C_{10}$-alkyl, particularly preferably $C_1$–$C_5$-alkyl, groups. Examples of alkyl groups are, in particular, methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl, etc.

The degree of branching and the number of carbon atoms in the terminal alkyl radicals $R^1$, $R^2$, $R^3$ and $R^4$ depend on the structure of the acyclic monoolefins in the hydrocarbon mixture used and on the activity of the catalyst. The activity of the catalyst also influences the extent of cross-metathesis (self-metathesis) of the acyclic olefins to form olefins which have novel structures and into which cyclopentene is then formally inserted in a ring-opening metathesis polymerization.

The oligomer mixtures of the formula I used according to the invention for the functionalization are obtainable by a metathesis reaction of hydrocarbon mixtures comprising acyclic and cyclic olefins.

Preferably used is a hydrocarbon mixture which results from the industrial processing of petroleum and which can, if required, be subjected beforehand to a partial catalytic hydrogenation to remove dienes. A particularly suitable example is a mixture ($C_5$ cut) which is enriched in saturated and unsaturated $C_5$ hydrocarbons. The $C_5$ cut can be obtained, for example, by subjecting the pyrolysis gasoline produced in the steam cracking of naphtha firstly to a selective hydrogenation, in order to convert the dienes and acetylenes present therein selectively into the corresponding alkanes and alkenes, and then to a fractional distillation, resulting in the $C_6$–$C_8$ cut, which is important for further chemical syntheses and which contains the aromatic hydrocarbons, as well as the $C_5$ cut used for the process for preparing the oligomer mixtures of the formula I.

The $C_5$ cut generally has a total olefin content of at least 30% by weight, preferably at least 40% by weight, in particular at least 50% by weight.

Suitable $C_5$ hydrocarbon mixtures in this connection are those with a total cyclopentene content of at least 5% by weight, preferably at least 10% by weight, in particular at least 12% by weight, and in general not more than 30% by weight, preferably not more than 20% by weight.

Furthermore, the proportion of pentene isomers in the acyclic monoolefins in suitable $C_5$ hydrocarbon mixtures is at least 70% by weight, preferably at least 80% by weight, in particular at least 90% by weight.

Preferably used for preparing the oligomer mixtures of the formula I is a $C_5$ cut produced industrially with a total olefin content of, for example, 50 to 60% by weight, such as about 56%, a cyclopentene content of, for example, 10 to 20%, such as about 15% by weight, and a pentene isomer content of, for example, 33 to 43% by weight, such as about 38% by weight, consisting of about 16% by weight n-pentene and about 22% by weight isomeric pentenes.

It is also possible furthermore to use a hydrocarbon mixture which comprises the $C_5$ cut and a petroleum fraction containing acyclic $C_4$ olefins (distillate 2) or the $C_5$ cut and ethene.

The metathesis reaction of the hydrocarbon mixture comprises a) disproportionation of the acyclic monoolefins in the hydrocarbon mixture ($C_5$ cut) by cross-metathesis, b) oligomerization of the cyclopentene by ring-opening metathesis, c) chain termination by reaction of the oligomers from b) with an acyclic olefin in the hydrocarbon mixture or a product from a), where steps a) and/or b) and/or c) may take place more than once on their own or in combination.

Step a)

Combinations of cross-metathesis of different, and self-metathesis of identical, acyclical olefins, and repetition of this reaction, result in a large number of monoolefins which differ in structure and number of carbons and which form the end groups of the oligomers of the formula I. The double bond content of the oligomers is also influenced by the proportion of cross-metathesis products, which increases with increasing activity of the catalyst used. Thus, for example, ethene is liberated in the self-metathesis of 1-pentene and may, where appropriate, escape as gas, which removes one double-bond equivalent from the reaction. At the same time there is an increase in the proportion of oligomers without terminal double bonds.

Step b)

The average number of cyclopentene insertions into the growing chain in the form of a ring-opening metathesis polymerization determines the average molecular weight of the cyclopentene oligomer mixture of the formula I which is formed. The average molecular weight of the oligomer mixtures of the formula I formed by the process according to the invention is preferably at least 274, which corresponds to an average number of three cyclopentene units per oligomer.

Step c)

Chain termination takes place by reaction of an oligomer which still has an active chain end in the form of a catalyst complex (alkylidene complex) with an acyclic olefin, with, in the ideal case, an active catalyst complex being recovered. The acyclic olefin in this case may be derived unchanged from the hydrocarbon mixture originally employed for the reaction, or have been previously modified in a cross-metathesis in stage a).

Suitable catalysts for the metathesis are known and comprise homogeneous and heterogeneous catalyst systems. The catalysts suitable for preparing oligomer mixtures of the formula I are generally based on a transition metal of group VIb, VIIb or VIII of the Periodic Table, preferred catalysts being based on Mo, W, Re and Ru.

Suitable homogeneous catalyst systems are generally transition metal compounds which are able, where appropriate in combination with a cocatalyst and/or where appropriate in the presence of the olefin precursors, to form a catalytically active metal carbene complex. Systems of this type are described, for example, by R. H. Grubbs in Comprehensive Organomet. Chem., Pergamon Press, New York, Volume 8, page 499 et seq. (1982).

Suitable catalyst/cocatalyst systems based on W, Mo and Re may, for example, comprise at least one soluble transition metal compound and an alkylating agent. These include, for example, $MOCl_2(NO)_2(PR_3)_2/Al_2(CH_3)_3Cl_3$; $WCl_6/BuLi$; $WCl_6/EtAlCl_2(Sn(CH_3)_4)/EtOH$; $WOCl_4/Sn(CH_3)_4$; $WOCl_2(O-[2,6-Br_2—C_6H_3])/Sn(CH_3)_4$; $CH_3ReO_3/C_2H_5AlCl_2$, and the last four mentioned are preferred for the process according to the invention.

Further transition metal alkylidene complexes suitable as metathesis catalysts are described by R. R. Schrock in Acc. Chem. Res., 23, (1990) 158 et seq. These are generally tetracoordinate Mo- and W-alkylidene complexes which additionally have two bulky alkoxy and one imido ligand. Preferably used for the process according to the invention are $((CH_3)_3CO)_2Mo(=N—[2,6-(i-C_3H_7)_2—C_6H_3])$ $(=CHC(CH_3)_2C_6H_5$ and $[(CH_3)_2C(CH_3)O]_2Mo(=N—[2,5-(i-C_3H_7)—C_6H_3])(=CH(CH_3)_2C_6H_5)$.

The catalysts particularly preferably used as homogeneous metathesis catalysts are those described in Angew. Chem. 107 (1995) 2179 et seq. in J. Am. Chem. Soc. 118 (1996) 100 et seq., and in J. Chem. Soc., Chem. Commun., (1995) 1127 et seq. These include, in particular, $RuCl_2(=CHR)(PR'_3)_2$, preferably $RUCl_2(=CHC_6H_5)$ $(P(C_6H_{11})_3)_2$, $(\eta^6\text{-p-cymene})RuCl_2(P(C_6H_{11})_3)/(CH_3)_3SiCHN_2$ and $(\eta^6\text{-p-cymene})RuCl_2(P(C_6H_{11})_3/C_6H_5CHN_2$. The two last-mentioned are generated in situ from one mol equivalent of $(\eta^6\text{-p-cymene})RuCl_2(P(C_6H_{11})_3)$ and 3 mol equivalents of diazoalkane $((CH_3)_3SiCHN_2$ or $C_6H_5CHN_2)$.

Suitable heterogeneous catalyst systems generally comprise a transition metal compound on an inert carrier, which compound is able to form a catalytically active alkylidene complex without cocatalyst, by reacting with the olefin precursors. Preferably used for this purpose are $Re_2O_7$ and $CH_3ReO_3$ on $Al_2O_3$ as carrier material.

The abovementioned homogeneous and heterogeneous catalyst systems differ greatly in their catalytic activity, especially with regard to cross-metathesis (step a)), and influence the product distribution in the cyclopentene-derived oligomer mixtures of the formula I. Thus, the ruthenium-based homogenous catalyst systems $RuCl_2(=CHC_6H_5)$ $(P(C_6H_{11})_3)_2$, $(\eta^6\text{-p-cymene})RuCl_2(P(C_6H_{11})_3)/(CH_3)_3SiCHN_2$ and $(\eta^6\text{-p-cymene})RuCl_2(P(C_6H_{11})_3)/C_6H_5CHN_2$ are particularly suitable.

In this connection, the first-mentioned ruthenium complex displays higher catalytic activity than the two last-mentioned, which, with reaction conditions which are otherwise the same, results in increased cross-metathesis, with liberation of ethene to some extent too, and the resulting cyclopentene-derived oligomer mixture of the formula I thus having a somewhat smaller proportion of double bonds, which is manifested, for example, by a lower iodine value. In addition, owing to the cross-metathesis, a larger number of acyclic olefins without terminal double bonds is available, so that using the first-mentioned homogeneous ruthenium catalyst results in more cyclopentene-derived oligomers of the formula I which have only one or no terminal double bond. The two last-mentioned ruthenium complexes have a somewhat lower catalytic activity than the one mentioned first, so that, using them in the process according to the invention, results in cyclopentene-derived oligomer mixtures of the formula I which have a higher proportion of double bonds and thus a higher iodine value and a larger proportion of terminal double bonds.

The heterogeneous catalyst systems also display the activity differences described above with the corresponding influence on the metathesis products. $CH_3ReO_3$ on $Al_2O_3$ as heterogeneous catalyst has a higher catalytic activity than the corresponding homogeneous catalyst system composed of $CH_3ReO_3/(C_2H_5)AlCl_2$.

It is thus possible if desired to obtain cyclopentene-derived oligomer mixtures of the formula I with varying proportions of double bonds and varying proportions of terminal double bonds, depending on the catalyst used.

The cyclopentene oligomers of the formula I obtained in the described process have an iodine value of at least 250 g $I_2/100$ g oligomers, preferably at least 300 g $I_2/100$ g oligomers. The average molecular weight of the cyclopentene-derived oligomers is at least 274 g/mol, which corresponds to an average conversion of three cyclopentene units per oligomer, assuming chain termination by an acyclic pentene (and not by a cross-metathesis product) in this case.

a) Hydroformylation

The process according to the invention for preparing functionalized cyclopentene-derived oligomer mixtures by reacting the previously described oligomers of the formula I which contain ethylenic double bonds comprises initially preparing hydroformylated oligomer mixtures by reacting the oligomer mixtures of the formula I with carbon monoxide and hydrogen in the presence of a hydroformylation catalyst.

Suitable catalysts for the hydroformylation are known and generally comprise a salt or a complex compound of an element of group VIII of the Periodic Table. Salts, and, in particular, complex compounds of rhodium or of cobalt are preferably used for the process according to the invention.

Examples of suitable salts are the hydrides, halides, nitrates, sulfates, oxides, sulfides or the salts with alkyl- or arylcarboxylic acids or alkyl- or arylsulfonic acids. Examples of suitable complex compounds are the carbonyl compounds and carbonyl hydrides of said metals, and complexes with amine, triarylphosphine, trialkylphosphine, tricycloalkylphosphine, olefins, or dienes as ligands. It is also possible to prepare catalyst systems in situ from the abovementioned salts and said ligands.

Suitable alkyl radicals in the ligands are the above-described linear or branched $C_1$–$C_{15}$-alkyl, in particular $C_1$–$C_5$-alkyl, radicals. Cycloalkyl is preferably $C_3$–$C_{10}$-cycloalkyl, in particular cyclopentyl and cyclohexyl, which may also be substituted by $C_1$–$C_4$-alkyl groups. Aryl is preferably phenyl (Ph) or naphthyl, which is unsubstituted or substituted by 1, 2, 3 or 4 $C_1$–$C_4$-alkyl, $C_1$–$C_4$-alkoxy, eg. methoxy, halogen, preferably chlorine, or hydroxyl, which may also be ethoxylated.

Suitable rhodium catalysts and catalyst precursors are rhodium(II) and rhodium(III) salts such as rhodium(III) chloride, rhodium(III) nitrate, rhodium(III) sulfate, potassium rhodium sulfate (rhodium alum), rhodium(II) and rhodium(III) carboxylate, preferably rhodium(II) and rhodium(III) acetate, rhodium(III) oxide, salts of rhodium (III) acid and trisammoniumhexachlororhodate(III).

Also suitable are rhodium complexes of the formula $RhX_mL^1L^2(L^3)_n$ where X is halide, preferably chloride or bromide, alkyl- or arylcarboxylate, acetylacetonate, aryl- or alkylsulfonate, in particular phenylsulfonate and toluenesulfonate, hydride or the diphenyltriazine anion, $L^1$, $L^2$, $L^3$ are, independently of one another, CO, olefins, cycloolefins, preferably cyclooctadiene (COD), dibenzophosphol, benzonitrile, $PR_3$ or $R_2P$-A-$PR_2$, m is 1, 2 or 3 and n is 0, 1 or 2. R (the R radicals can be identical or different) means alkyl, cycloalkyl and aryl radicals, preferably phenyl, p-tolyl, m-tolyl, p-ethylphenyl, p-cumyl, p-t-butylphenyl, p-$C_1$–$C_4$-alkoxyphenyl, preferably p-anisyl, xylyl, mesityl, p-hydroxyphenyl, which may also be in ethoxylated form, isopropyl, $C_1$–$C_4$-alkoxy, cyclopentyl or cyclohexyl. A is 1,2-ethylene or 1,3-propylene. $L^1$, $L^2$ or $L^3$ are, independently of one another, preferably CO, COD, P(phenyl)$_3$, P(i-propyl)$_3$, P(anisyl)$_3$, P(OC$_2$H$_5$)$_3$, P(cyclohexyl)$_3$, dibenzophosphol or benzonitrile. X is preferably hydride, chloride, bromide, acetate, tosylate, acetylacetonate or the diphenyltriazine anion, in particular hydride, chloride or acetate.

Particularly preferred rhodium complexes are Rh(CO)$_2$acac and the rhodium carbonyl compounds such as tetrarhodium dodecacarbonyl or hexarhodium hexadecacarbonyl, which are used alone or together with phosphines. An Rh(CO)$_2$acac/P(phenyl)$_3$ catalyst is particularly preferably used, the molar ratio of the amounts Rh(CO)$_2$acac to P(phenyl)$_3$ being about 1:2 to 1:10.

Examples of suitable cobalt compounds are cobalt(II) chloride, cobalt(II) sulfate, cobalt(II)nitrate, their amine or hydrate complexes, cobalt carboxylates, such as cobalt acetate, cobalt ethylhexanoate, cobalt naphthoate and the carbonyl complexes of cobalt such as dicobalt octacarbonyl, tetracobalt dodecacarbonyl and hexacobalt hexadecacarbonyl. Preferably used for the process according to the invention are the cobalt carbonyl complexes and, in particular, dicobalt octacarbonyl.

Said compounds of rhodium and cobalt are known in principle and are adequately described in the literature or they can be prepared by the skilled worker in a similar way to the compounds already known. This preparation may also take place in situ, in which case the catalytically active species can also be formed from the abovementioned compounds as catalyst precursors only when the hydroformylation conditions are applied.

The hydroformylation catalyst is generally used in amounts of from 1 to 150 ppm, preferably 1 to 100 ppm. The reaction temperature is generally in the range from room temperature to 200° C., preferably 50 to 150° C.

The reaction can be carried out under a pressure of from about 10 to 650 bar.

It is possible according to the invention to use as hydroformylation catalyst a Rh(CO)$_2$acac/P(phenyl)$_3$ catalyst where the molar ratio of the amounts of Rh(CO)$_2$acac to P(phenyl)$_3$ is about 1:2 to 1:10, preferably about 1:3 to 1:7. Compared with hydroformylation catalysts without phosphine substituents, rhodium-triphenylphosphine catalysts permit reactions to be carried out at lower temperatures and under lower pressures, with involvement preferably only of terminal double bonds. The reaction temperature with this catalyst system is about 80 to 120° C. under a pressure of about 1 to 30 bar.

The H$_2$:CO molar ratio of amounts is generally about 1:5 to about 5:1.

The invention furthermore relates to the hydroformylated cyclopentadiene-derived oligomer mixtures obtained by the process according to the invention. The resulting hydroformylated oligomers have a carbonyl value of, preferably, at least 150 mg, in particular 250 mg, KOH/g product preferably at least 300 mg KOH/g product. It is preferred for most of the ethylenic double bonds present in the precursor to be converted by the hydroformylation into aldehydes or, as stated hereinafter, where appropriate also into alcohols, so that the iodine value of the hydroformylated oligomers is preferably ≦60 g I$_2$/100 g oligomers.

The hydroformylated oligomers are advantageously liquid, owing to their lower degree of polymerization, and, in contrast to the hydroformylated polypentenamers described in the Journal of Polymer Science, Polymer Chemistry Edition 18 (1980) 781 et seq., show less of a tendency to crosslinking. The hydroformylation products thus retain their solubility in organic solvents.

The invention further relates to the use of the hydroformylated cyclopentene-derived oligomer mixtures as intermediates for further processing by functionalization of at least some of the aldehyde functionalities present therein.

The hydroformylated oligomer mixtures are furthermore suitable for modifying polymers, eq. as crosslinkers, as additives in leather tanning, and as biocides.

b) Oxo Carboxylic Acids

The invention further relates to a process for preparing cyclopentene-derived oligomer mixtures with carboxyl functionalities, where the previously described hydroformylated oligomer mixtures are reacted in the presence of an oxidizing agent.

It is generally possible to use a large number of different oxidizing agents and processes for oxidizing aldehydes to carboxylic acids, as described, for example, in J. March, Advanced Organic Chemistry, published by John Wiley & Sons, 4th Edition, page 701 et seq. (1992). Examples include oxidation with permanganate, chromate, etc. In a preferred embodiment of the process according to the invention, atmospheric oxygen is used to oxidize the hydroformylated cyclopentene-derived oligomer mixtures. Oxidation with air can take place either catalytically in the presence of metal salts or else in the absence of catalysts. The metals preferably employed are those able to change valency, such as Cu, Fe, Co, Mn etc. Preferably no catalyst is used in the process according to the invention. Oxidation with atmospheric oxygen can take place in a neutral or acidic medium and preferably takes place in the process according to the invention in an alkaline medium with addition of a base such as NaOH, KOH etc. It is easily possible in atmospheric oxidation to control the conversion by the reaction time. The oligomer mixtures with carboxyl functionalities preferably obtained on use of an oxygen-containing gas as oxidizing agent have an acid value of at least 50 mg KOH/g product, preferably at least 70 mg KOH/g product.

In another preferred embodiment of the process according to the invention, an aqueous hydrogen peroxide solution is used in combination with a carboxylic acid, preferably acetic acid, as oxidizing agent. This results in oligomer mixtures with carboxyl functionalities with the acid value being at least 150 mg KOH/g product, preferably at least 200 mg KOH/g product.

The invention further relates to cyclopentene-derived oligomer mixtures with carboxyl functionalities which can be obtained by the processes described above. Their acid value is, as described above, at least 50 mg KOH/g product, but preferably at least 70 mg KOH/g product, depending on the reaction procedure.

The invention further relates to the use of the oligomer mixtures with carboxyl functionalities, which may also be esterified, in particular with C$_1$–C$_{18}$ alkanols, for preparing copolymers, as complexing agents, eg. as incrustation inhibitors, as surfactant component, as concrete plasticizer and for sea water desalination.

c) Oxo Alcohols

The invention further relates to a process for preparing cyclopentene-derived oligomer mixtures with hydroxyl functionalities, where the hydroformylated oligomer mixtures from stage a) are reacted with hydrogen in the presence of a hydrogenation catalyst.

Suitable hydrogenation catalysts are generally transition metals such as Cr, Mo, W, Fe, Rh, Co, Ni, Pd, Pt, Ru etc., or mixtures thereof, which may be applied, to increase the activity and stability, to carriers such as active carbon, alumina, kieselguhr etc. To increase the catalytic activity, Fe, Co and, preferably, Ni can also be used in the form of the Raney catalysts as metal sponge with a very large surface area.

Preferably used as catalyst for the process according to the invention for preparing oligomer mixtures with hydroxyl functionalities is Raney nickel.

The hydrogenation of the oxo aldehydes from stage a) preferably takes place at elevated temperatures under elevated pressure, depending on the activity of the catalyst. When Raney nickel is used as catalyst, the reaction is carried out at about 80 to 150° C. under a pressure of about 50 to 350 bar.

In a particular embodiment of the process according to the invention, the preparation of the oligomer mixtures with hydroxyl functionalities takes place together with the hydroformylation in a one-stage reaction. This is done by reacting the cyclopentene-derived oligomer mixtures with ethylenic double bonds of the formula I with carbon monoxide and hydrogen in the presence of a hydroformylation catalyst which is also suitable for the further hydrogenation to give the oxo alcohols. In principle, all hydroformylation catalysts are also suitable for catalytic hydrogenations, but generally higher temperatures and/or higher pressures and/or longer reaction times, and a larger amount of catalysts, depending on the catalytic activity, are used than for hydroformylation on its own.

All the catalysts described in stage a) are suitable for the process according to the invention for hydroformylation with simultaneous hydrogenation. A cobalt carbonyl catalyst is preferably used, in particular $Co_2(CO)_8$. The reaction is generally, carried out at from 100 to 220° C., preferably 150 to 200° C., under a pressure of from 50 to 650 bar, preferably 100 to 600 bar.

Other processes can also be used to reduce the oxo aldehydes to the alcohols. These include, for example, reduction with complex hydrides such as $LiAlH_4$ and $NaBH_4$, reduction with sodium in ethanol by the Bouveault-Blanc method, and other known processes.

The invention further relates to the cyclopentene-derived oligomer mixtures with hydroxyl functionalities obtained by one of the two processes described above. Conversion is preferably as complete as possible, ie. reduction is as complete as possible so that the carbonyl value of the oxo alcohols obtained by the process according to the invention is small by comparison with the carbonyl value of the oligomeric oxo aldehydes employed as precursor. The maximum carbonyl value of the oxo alcohols is generally 20. The alcohol value is at least 150 mg KOH/g product, in particular 250 mg KOH/g product, preferably at least 300 mg KOH/g product.

The invention further relates to the use of the cyclopentene-derived oligomer mixtures according to the invention with hydroxyl functionalities, where appropriate after alkoxylation (etherification) or esterification thereof, in particular with a $C_1$–$C_{18}$ carboxylic acid, as plasticizer, reactive thinner, antifoam, adhesive additive and as polyol component for preparing polyurethanes.

d) Amine Synthesis

Hydrogenation of aldehydes and ketones in the presence of ammonia, primary or secondary amines results, through reductive amination, in the corresponding primary, secondary or tertiary amines, and intramolecular crosslinking with amino groups already converted. The invention thus relates further to a process for preparing cyclopentene-derived oligomer mixtures with amino functionalities, where the hydroformylated oligomer mixtures from stage a) or the oligomer mixtures with hydroxyl functionalities from stage c) are reacted with ammonia, a primary or secondary amine in the presence of an amination catalyst and of hydrogen.

The hydroformylated oligomer mixtures are preferably reacted with ammonia in the presence of hydrogen and a hydrogenation catalyst, resulting in oligomer mixtures with primary amino functionalities.

The preparation of amines from aldehydes or ketones can generally be carried out as a one-stage or two-stage process. In the two-stage variant, firstly a condensate is formed from ammonia, primary or secondary amines on the one hand and aldehydes on the other hand in a first reaction step, and is then hydrogenated in a second reaction step.

In a suitable embodiment of the two-stage process, the hydroformylated oligomer mixtures from stage a) are reacted with ammonia or amines of the formula R-$NH_2$ where R is $NH_2$, $C_1$–$C_{10}$-alkyl, $C_6$–$C_{20}$-aryl, $C_7$–$C_{20}$-arylalkyl, $C_7$–$C_{20}$-alkylaryl or an organosilicon residue having 3 to 30 carbon atoms, or with a reagent which liberates ammonia or amines, and subsequently hydrogenated.

Examples of suitable R radicals in the amines R-$NH_2$ are $NH_2$, the alkyl radicals mentioned above for the oligomers of the formula I, phenyl, naphthyl, p-tolyl, o-tolyl, xylyl and tri($C_1$–$C_{10}$)alkyl-silyl such as trimethylsilyl, tert-butyldimethylsilyl or else triarylsilyl, for example triphenylsilyl, tri-p-tolylsilyl or trinaphthylsilyl.

Suitable reagents which liberate ammonia are in general all ammonium salts, preferably ammonium carbonate. Ammonium carbonate and, in particular, ammonia are preferably used for the two-stage process according to the invention.

The process according to the invention for preparing oligomer mixtures with amino functionalities is preferably carried out as one-stage process, in which case the hydroformylated oligomer mixtures from stage a) are reacted with ammonia, a primary or secondary amine in the presence of an amination catalyst and of hydrogen.

The hydroformylated oligomer mixtures are preferably reacted with ammonia in the presence of hydrogen and of an amination catalyst. Suitable amination catalysts for the one-stage and the two-stage process are the hydrogenation catalysts described above in stage c), preferably copper, cobalt or nickel in the form of the Raney metals or on a carrier, and platinum.

Particularly suitable amination catalysts are the catalysts described in EP-A 394 842 and in DE-A 4 429 547 for hydrogenation of unsaturated compounds, which are incorporated herein by reference. This catalyst has, in the non-reduced oxide form, a content of from 20 to 75% by weight of nickel oxide, 10 to 75% by weight of zirconium dioxide and 5 to 50% by weight of copper oxide, with or without up to 5% by weight of molybdenum oxide and with or without up to 10% by weight of manganese oxide. Before being used according to the invention, the catalyst is subjected to a reductive treatment with hydrogen at from 180 to 300° C. for from 5 to 30 hours under a hydrogen pressure of from 1 to 300 bar. The hydrogenation catalyst particularly used for the process according to the invention comprises 51% by weight NiO, 17% by weight CuO, 31% by weight $ZrO_2$ and 1% by weight $MoO_3$, based on the non-reduced oxide catalyst.

The reductive amination using the catalyst described above is carried out at from about 100 to 250° C., preferably 150 to 230° C., under a pressure of from about 100 to 300 bar, preferably from 150 to 250 bar.

It is possible if desired also to use other reduction processes to prepare the cyclopentene-derived oligomer mixtures according to the invention with amino functionalities from the oxo aldehydes of stage a). These include, for example, reductive amination of aldehydes in the presence of formic acid by the Leuckart-Wallach method, and other processes known to the skilled worker.

The invention further relates to the cyclopentene-derived oligomer mixtures with amino functionalities obtained by the process according to the invention. Conversion in the reductive amination in stage d) is preferably as complete as possible so that the resulting products have a small carbonyl value of, preferably, less than 20. The side reaction with formation of alcohols due to the oxo aldehydes undergoing reduction exclusively is of only minor importance in the process according to the invention so that products with an alcohol value of less than 40 mg KOH/g product are obtained. The amine value is at least 150 mg KOH/g product, preferably at least 200 mg KOH/g product. The tertiary amine content is moreover low with an amine value not exceeding 20 mg KOH/g product.

The invention further relates to the use of the cyclopentene-derived oligomer mixtures with amino functionalities according to the invention as component in epoxy resins, polyamides, polyurethanes, polyureas, as dispersant, dye transfer inhibitor, paper auxiliary, soil remover, component in skin creams and hair-care compositions, crosslinker for adhesives, stabilizer for polyoxymethylene, corrosion inhibitors, textile assistants, auxiliaries for dispersions, adhesives, protective colloids, adhesive coatings, epoxy hardeners in aqueous dispersions, auxiliaries for dishwashing compositions, paper auxiliaries, leveling agents for textiles, solubilizers for cosmetics, for metal extraction, comlexing agents, fuel additive, lubricants, corrosion inhibitor for aqueous systems, addition to glue and resin raw materials, dye fixation on textiles, paper fixation, retention, complexing agent for metal recycling, stabilizer for hydroxylamine, surfactants.

The invention is illustrated by means of the following non-restrictive examples.

EXAMPLE

The gas chromatograms were recorded using a Hewlett Packard 5890 gas chromatograph with a DB 5.30 m×0.32 mm glass capillary column and a flame ionization detector with attached integration unit.

The iodine value is defined as g iodine/100 g product and was measured by the Kaufmann method in which about 0.2 g of test substance are weighed accurately into a 300 ml Erlenmeyer flask and dissolved in 20 ml of chloroform and, after addition of exactly 20.00 ml of bromine solution, left to stand in the dark for 2 hours. Then 10 ml of potassium iodide solution and about 2 g of potassium iodate are added. The iodine which separates out is titrated against standard sodium thiosulfate solution using starch solution as indicator until the blue color disappears. To prepare the bromine solution used in the Kaufmann method, 120 g of sodium bromide are dissolved in about 900 ml of methanol. 6.5 ml of bromine are added to this, and the volume is made up to 1000 ml with methanol. The solution is then about 0.25 molar and is stored in brown glass bottles.

The carbonyl value is defined as mg KOH/g product. For the determination, about 1.5 g of test substance are weighed accurately and 10 ml of toluene, 50 ml of hydroxylammonium chloride solution and 5 ml of 0.5 N HCl are added. The solution is stirred at room temperature for 24 hours and titrated potentiometrically against standard sodium hydroxide solution to the turning point. The hydroxylammonium chloride solution is prepared by dissolving 70 g of hydroxylammonium chloride in 320 ml of water, making up to 2 l with ethanol and adjusting to pH 2.5 with HCl.

The acid value is defined as mg KOH/g product and was determined by the DIN 53402 method or the method in the Deutsche Arzneibuch 10 V. 3.4.1. (1993).

The alcohol value is defined as mg KOH/g product. For the determination, about 1 g of test substance is weighed accurately and, after addition of 9.8 ml of acetylating reagent, left to stand at room temperature for 24 hours. Then 25 ml of distilled water are added and the mixture is stirred for 15 min, 25 ml of isopropanol are added and the mixture is titrated potentiometrically against standard sodium hydroxide solution to the turning point. The acetylating reagent is prepared by mixing 810 ml of pyridine, 100 ml of acetic anhydride and 9 ml of acetic acid.

The amine value is defined as mg KOH/g product. For the determination, about 1.0 g of test substance is weighed accurately, dissolved in 50 ml of acetic acid and titrated potentiographically against 0.1 molar standard trifluoromethane-sulfonic acid solution in acetic acid. The method is described in Huber, Titrationen in nichtwäBrigen Lösungsmitteln, Akademisch Verlagsgesellschaft, Frankfurt a. M. page 130 et seq. (1964) and in Gyenes, Titrationen in nichtwäBrigen Medien, Ferdinand Enke Verlag, Stuttgart, page 488 et seq. (1970).

The tertiary amine value is defined as mg KOH/g product. For the determination, about 1.0 g of test substance is weighed accurately and dissolved in ml of acetic acid and, after addition of 30 ml of acetic anhydride, heated on a water bath at 70° C. for 2 hours. After cooling to room temperature, the solution is titrated potentiographically against 0.1 molar standard trifluoromethanesulfonic acid solution in acetic acid. The method is described in Huber, Titrationen in nichtwäBrigen Lösungsmitteln, Akademische Verlagsgesellschaft, Frankfurt a. M., page 147 et seq. (1964) and in Gyenes, Titrationen in nichtwäBrigen Medien, Ferdinand Enke Verlag, Stuttgart, page 574 et seq. (1970).

I. Preparation of Cyclopentene-derived Oligomer Mixtures of the Formula I

Example 1

A 1:1 mixture of 17.1 mol each of cyclopentene and 1-pentene was mixed at room temperature under atmospheric pressure with a catalyst mixture generated in situ from 8.6 mmol of (p-cymene)RuCl$_2$(PCy$_3$) and 2 ml of Me$_3$SiCHN$_2$ in 50 ml of CH$_2$Cl$_2$.

Slight evolution of gas was observed during this. After stirring for 3 hours, the solution was chromatographed on neutral Al$_2$O$_3$, and the colorless filtrate was distilled to remove unreacted low boilers. The remaining colorless, low-viscosity liquid weighed 956 g and had the following composition (GC percent areas): 26% C$_{10}$H$_{18}$, 22% C$_{15}$H$_{26}$, 17% C$_{20}$H$_{34}$, 13% C$_{25}$H$_{42}$, 10% C$_{30}$H$_{50}$, 7% C$_{35}$H$_{58}$, 5% C$_{40}$H$_{66}$.

Iodine value: 351 g I$_2$/100 g

Example 2

1 l of C$_5$ cut (cyclopentene content: 15%) was reacted at room temperature under atmospheric pressure with a solution of 0.6 mmol of RuCl$_2$(=CHPh)(PCy$_3$)$_2$ in 20 ml of CH$_2$Cl$_2$. Slight evolution of gas was observed during this. After stirring for 1 h, the solution was chromatographed on Al$_2$O$_3$, and the colorless filtrate was distilled to remove unreacted low boilers. 96 g of a colorless, low-viscosity liquid of the following composition (GC percent areas) were obtained:

4% C$_7$H$_{12}$, 11% C$_8$H$_{16}$, 14% C$_{10}$H$_{18}$, 3% C$_{12}$H$_{20}$, 8% C$_{13}$H$_{24}$, 12% C$_{15}$H$_{26}$, 2% C$_{17}$H$_{28}$, 5% C$_{18}$H$_{32}$, 9% C$_{20}$H$_{34}$, 1% C$_{22}$H$_{36}$, 4% C$_{23}$H$_{40}$, 7% C$_{25}$H$_{42}$, 3% C$_{28}$H$_{48}$, 6% C$_{30}$H$_{50}$, 1% C$_{33}$H$_{56}$, 4% C$_{35}$H$_{58}$, 3% C$_{40}$H$_{58}$, 3% C$_{40}$H$_{66}$, 2% C$_{40}$H$_{66}$, 1% C$_{40}$H$_{66}$.

Iodine value: 329 g $I_2$/100 g

Example 3

A 1:1 mixture of cyclopentene and 1-pentene was pumped continuously into a tubular reactor charged with $Re_2O_7$/$Al_2O_3$ at 60° C. under 5 bar and with residence times of 1–3 h. The reaction product was then separated into a low-boiling fraction and a high-boiling fraction in a falling film evaporator operated at 115° C. under atmospheric pressure, and the former was returned to the metathesis process. The high-boiling fraction was freed of residues of low boilers under reduced pressure. With space-time yields of 50–500 g $l^{-1}$ $h^{-1}$, pale yellow liquids were obtained and were finally chromatographed on $Al_2O_3$. A sample had the following composition (GC percent areas):

3% $C_7H_{12}$, 9% $C_8H_{16}$, 16% $C_{10}H_{18}$, 2% $C_{12}H_{20}$, 8% $C_{13}H_{24}$, 13% $C_{15}H_{26}$, 2% $C_{17}H_{28}$, 6% $C_{18}H_{32}$, 11% $C_{20}H_{34}$, 1% $C_{22}H_{36}$, 4% $C_{23}H_{40}$, 9% $C_{25}H_{42}$, 2% $C_{28}H_{48}$, 6% $C_{30}H_{50}$, 3% $C_{35}H_{58}$, 2% $C_{40}H_{66}$, 1% $C_{40}H_{66}$, 1% $C_{45}H_{74}$.

Iodine value: 349 g $I_2$/100 g

Example 4

1 l of $C_5$ cut was pumped continuously into a tubular reactor charged with $Re_2O_7$/$Al_2O_3$ at 60° C. under 5 bar and with residence times of 1–3 h. The reaction product was separated into a low-boiling fraction and a high-boiling fraction in a falling film evaporator operated at 115° C. under atmospheric pressure. The latter fraction was distilled under reduced pressure to remove residues of low boilers. With space-time yields of 20–100 g $l^{-1}$ $h^{-1}$ and cyclopentene conversions up to 70%, pale yellowish liquids were obtained and were finally chromatographed on $Al_2O_3$. A sample had the following composition (GC percent areas):

4% $C_7H_{12}$, 11% $C_8H_{16}$, 14% $C_{10}H_{18}$, 3% $C_{12}H_{20}$, 8% $C_{13}H_{24}$, 12% $C_{15}H_{26}$, 2% $C_{17}H_{28}$, 5% $C_{18}H_{32}$, 9% $C_{20}H_{34}$, 1% $C_{22}H_{36}$, 4% $C_{23}H_{40}$, 7% $C_{25}H_{42}$, 3% $C_{28}H_{48}$, 6% $C_{30}H_{50}$, 1% $C_{33}H_{56}$, 4% $C_{35}H_{58}$, 3% $C_{40}H_{66}$, 2% $C_{45}H_{74}$, 1% $C_{50}H_{82}$.

Iodine value: 325 g $I_2$/100 g

II. Hydroformylation (Rhodium-catalyzed)

Examples 5–9

1000 g of an oligomer from one of Examples 1–3 and a catalyst, with or without solvent as shown in Table 1, were introduced into a 2000 ml autoclave. The autoclave was heated to the temperature stated in Table 1, increasing the pressure to the value stated in Table 1 by passing in a carbon monoxide/hydrogen mixture (molar ratio 1:1). The pressure in the autoclave fell due to reaction of part of the gas mixture and was maintained by passing in further hydrogen/carbon monoxide mixture until the pressure was constant for 3 hours. After the required reaction time, the heating and gas introduction were switched off and the cooled autoclave was emptied through a rising tube into a storage vessel.

The degree of hydroformylation is characterized by the analytical results (carbonyl value, iodine value) indicated in Table 1.

TABLE 1

Rhodium-catalyzed hydroformylation

| Example No. | Oligomer from Example | Precursor iodine value | Catalyst; amount of metal relative to oligomer | Pressure (bar) | Temp. (° C.) | Solvent | Product carbonyl value | Product iodine value |
|---|---|---|---|---|---|---|---|---|
| 5 | 1 | 351 | $Rh(CO)_2acac$; 5 ppm | 600 | 130 | — | 430 | 37 |
| 6 | 1 | 351 | $Rh(CO)_2acac$; 10 ppm | 600 | 130 | — | 495 | <1 |
| 7 | 2 | 329 | $Rh(CO)_2acac$; 20 ppm | 280 | 130 | — | 307 | 51 |
| 8 | 3 | 349 | $Rh(CO)_2acac$; 100 ppm | 280 | 130 | 50% toluene | 349 | 3 |
| 9 | 1 | 351 | $Rh(CO)_2acac$ (100 ppm)/TPP[1] Molar ratio TPP/Rh = 5:1 | 20 | 100 | — | 15 | |

[1]TPP = triphenylphosphine

Examples 5 and 6 under 600 bar show by comparison with Examples 7 and 8 under 280 bar a high selectivity for the conversion of C=C double bonds into the corresponding aldehyde compounds. Under 280 bar there is a higher proportion of hydrogenation and not hydroformylation.

III. Oxo Carboxylic Acid Synthesis

Example 10

Oxidation with Atmospheric Oxygen 1200 g of the hydroformylated oligomer from Example 8 were introduced with 1200 g of toluene into a heatable vessel with a volume of 3 l. Then 2.5 g of potassium hydroxide were added. The temperature was raised to 40° C. and then introduction of air was started, and samples were taken at intervals. The conversion or the result of oxidation was measured by determining the acid value. The reaction was stopped after 120 hours. The results of the oxidation are shown in Table 2.

TABLE 2

Oxidation of the hydroformylated oligomer from Example 8

| Example No. | Time (h) | Product acid value |
|---|---|---|
| 10 | 24 | 70 |
|  | 48 | 154 |
|  | 120 | 179 |

Example 11

Oxidation with Hydrogen Peroxide/glacial Acetic Acid 100 g of hydroformylated oligomer from Example 7 were introduced into a flask and cooled to 5° C. in an icebath. A mixture of 100 ml of 30% strength aqueous acetic acid and 100 ml of 30% strength aqueous hydrogen peroxide solution was added dropwise over the course of 7 hours, followed by stirring for one hour. The product was separated from the aqueous phase in a separating funnel, and the organic phase was washed three times with water until neutral and then dried over sodium sulfate. The result of oxidation was measured by determining the acid value. It was 214 mg of KOH/g.

IV. Oxo Alcohol Synthesis

Example 12

Hydroformylation (Cobalt-catalyzed) at Elevated Temperature 1000 g of the oligomer from Example 4 were introduced with 0.13% by weight of $Co_2(CO)_8$, based on the oligomer, into a 2000 ml autoclave. The autoclave was heated to 185° C. while the pressure was raised to 280 bar by passing in a carbon monoxide/hydrogen mixture (molar ratio 1:1). The pressure in the autoclave fell due to reaction of part of the gas mixture and was maintained by passing in further hydrogen/carbon monoxide mixture until the pressure was constant for 3 hours. After 10.5 hours, the heating and the gas introduction were switched off and the cooled autoclave was emptied through a rising tube into a storage vessel.

The discharge was stirred with 500 ml of 10% strength aqueous acetic acid at 100° C. while passing in air for 30 min. Two phases resulted, the lower one being the cobalt-containing water/acetic acid mixture. The latter was separated off. The organic phase was washed twice with 500 ml of water each time and dried. The degree of hydroformylation and the degree of reduction were determined from the analytical results (carbonyl value, alcohol value), which are shown in Table 3.

V. Amine Synthesis

Activation of the amination catalyst (disclosed in EP-A-194 842: 51% by weight NiO, 17% by weight CuO, 31% by weight $ZrO_2$, 1% by weight $MoO_3$):

The previously reduced and passivated catalyst (pellets) was introduced into an autoclave, which was tested for leaks under a pressure of 20 bar for hydrogen and was then heated to 200° C., a pressure of about 30 to 39 being set up. This was increased to 100 bar with hydrogen, and the catalyst was activated at 200° C. for 16 h, followed by cooling and decompression. The pressure vessel was evacuated and the precursor, where appropriate in a suitable solvent, eg. THF, was sucked in with exclusion of air, and nitrogen was admitted.

General method for the amination/reductive amination

After activation of the catalyst as described above, the precursor (hydroformylated oligomer from Example 7) was transferred into the evacuated autoclave, nitrogen was admitted, the amount of ammonia indicated in Table 5 and 30 bar of hydrogen were injected, the mixture was heated to the final temperature indicated, hydrogen was injected to the final pressure indicated, and the reaction was carried out for the indicated time. This was followed by cooling, decompression and removal of the contents of the autoclave using a suitable solvent, eg. THF.

TABLE 3

Result of the cobalt-catalyzed hydroformylation

| Example No. | Oligomer from Example | Precursor iodine value | Catalyst; amount of metal relative to oligomer | Pressure (bar) | Temp. (° C.) | Product carbonyl value | Product iodine value | Product alcohol value |
|---|---|---|---|---|---|---|---|---|
| 12 | 4 | 325 | $Co_2(CO)_8$; 0.13% | 280 | 130 | 8 | 3 | 285 |

Example 13

2800 g of a hydroformylated oligomer from Example 5 were introduced with 50 g of Raney nickel into a 5 l stirred autoclave. The pressure was then adjusted with hydrogen to 280 bar and the temperature was adjusted to 125° C. The pressure in the autoclave fell due to reaction of part of the gas and was maintained by passing in further hydrogen until (10 h) the pressure was constant for 3 hours. The heating and the gas introduction were then switched off and the cooled autoclave was emptied into a storage vessel. The discharge was filtered to remove Raney nickel.

The result of hydrogenation was determined from the analytical e results (carbonyl value, alcohol value) which are shown in Table 4.

TABLE 4

Hydrogenation of an oxo aldehyde

| Example No. | Hydroformylated oligomer from Example No. | Precursor carbonyl value | Product carbonyl value | Product alcohol value |
|---|---|---|---|---|
| 13 | 5 | 430 | 7 | 347 |

Example 14

15 ml of the catalyst were reduced in a stirred autoclave (300 ml) with catalyst basket at 200° C. and 100 bar for 16 h as described above, the autoclave was charged with 50 g of 30% strength solution of hydroformylated cyclopentene oligomer from Example 7 in THF, and reaction was carried out with 73 ml of $NH_3$ at 185° C. and 200 bar for 20 h as described above. Removal was carried out as described with THF.

After removal of the THF in a rotary evaporator, 18.3 g of a colorless liquid product were obtained. The reaction conditions and analytical results are shown in Table 5.

Example 15

15 ml of the catalyst were reduced in a stirred autoclave (300 ml) with catalyst basket at 200° C. and 100 bar for 16 h as described above, the autoclave was charged with 60 ml of 50% strength solution of hydroformylated cyclopentene oligomer from Experiment 8 in THF, and reaction was carried out with 50 ml of $NH_3$ at 200° C. and 220 bar for 20 h as described above. Removal was carried out as described with THF.

After removal of the THF in a rotary evaporator, 20.3 g of a colorless liquid product were obtained. The reaction conditions and analytical results are shown in Table 5.

Example 16

150 ml of the catalyst were reduced in a 2.5 l stirred autoclave with catalyst basket at 200° C. and 100 bar for 16 h as described above, the autoclave was charged with 600 ml of 50% strength solution of hydroformylated cyclopentene oligomer from Experiment 8 in THF, and reaction was carried out with 500 ml of $NH_3$ at 200° C. and 220 bar for 20 h as described above. Removal was carried out with THF and, after removal of the solid constituents by filtration and removal of the THF in a rotary evaporator to a volume of about 500 ml, the residue was mixed with 300 ml of toluene and evaporated in a rotary evaporator.

314 g of a colorless liquid product were obtained. The reaction conditions and analytical results are shown in Table 5.

TABLE 5

| | Amination | | | | | | | |
|---|---|---|---|---|---|---|---|---|
| Ex. No. | Precursor: $NH_3$ stoichiometry | Temp. [° C.] | Pressure [bar] | Time [h] | OH value | CO value | A-mine value | tert. A-mine value |
| Precursor from Ex. 7 | | | | | 27 | 307 | 0 | 0 |
| 14 | 1:25 | 185 | 200 | 20 | 33 | 3 | 252.7 | 7 |
| 15 | 1:10 | 200 | 220 | 20 | <1 | <1 | 231.5 | 9.9 |
| 16 | 1:10 | 200 | 220 | 48 | 15 | | 264 | 12.4 |

We claim:

1. A process for preparing functionalized cyclopentene-derived oligomer mixtures by a single stage or multistage functionalization of at least some of the ethylenic double bonds present in an oligomer mixture of the formula I $$R^1R^2C=CH-(CH_2)_3-CH]_nCH^3R^4 \tag{I}$$

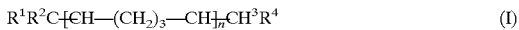

where n is an integer from 1 to 15, and $R^1$, $R^2$, $R^3$ and $R^4$ are, independently of one another, hydrogen or alkyl, wherein the oligomer mixtures of the formula I are obtained by a metathesis reaction of a hydrocarbon mixture comprising acyclic and cyclic olefins, and wherein said hydrocarbon mixture is a $C_5$-hydrocarbon mixture with a total cyclopentene content of at least 5% by weight and a proportion of pentene isomers in the acyclic monoolefins of at least 70% by weight, and wherein the oligomer mixtures of formula I are subjected to a hydroformylation to obtain a hydroformylated oligomer mixture and, optionally, further functionalization selected from:

reaction in the presence of an oxidizing agent to obtain an oligomer mixture with carboxyl functionalities, reaction with hydrogen in the presence of a hydrogenation catalyst to obtain an oligomer mixture with hydroxyl functionalities, reaction with ammonia, or a primary or secondary amine in the presence of an amination catalyst and of hydrogen to obtain an oligomer mixture with amino functionalities.

2. A process as defined in claim 1, wherein the oligomer mixture of the formula I is hydroformylated with carbon monoxide and hydrogen in the presence of a hydroformylation catalyst.

3. A hydroformylated cyclopentene-derived oligomer mixture obtained by a process as defined in claim 2.

4. A cyclopentene-derived oligomer mixture with carboxyl functionalities obtained by a process as claimed in claim 1.

5. A process as defined in claim 1 for preparing cyclopentene-derived oligomer mixtures with hydroxyl functionalities, wherein the hydroformylated oligomer mixture is reacted with hydrogen in the presence of a hydrogenation catalyst.

6. The process as defined in claim 5, wherein said hydrogenation catalyst is a metal of group VIII or IB of the Periodic Table of the Elements.

7. A cyclopentene-derived oligomer mixture with hydroxyl functionalities, obtained by a process as defined in claim 1.

8. A cyclopentene-derived oligomer mixture with amino functionalities obtained by a process as defined in claim 1.

9. A process as claimed in claim 1, wherein the cyclopentene-derived oligomer mixture with carboxy functionalities is esterified with a $C_1-C_{18}$-alkanol.

10. An ester of a cyclopentene-derived oligomer mixture with carboxyl functionalities with a $C_1-C_{18}$-alkanol obtained by a process as claimed in claim 9.

11. A process as claimed in claim 1, wherein the cyclopentene-derived oligomer mixture with hydroxyl functionalities is etherified to yield an $C_1-C_{18}$-alkyl ether thereof.

12. A $C_1-C_{18}$-alkyl ether of a cyclopentene-derived oligomer mixture with hydroxyl functionalities obtained by a process as claimed in claim 11.

13. A process as claimed in claim 1, wherein the cyclopentene-derived oligomer mixture with hydroxyl functionalities is esterified with a $C_1-C_{18}$-carboxylic acid.

14. An ester of a cyclopentene-derived oligomer mixture with hydroxyl functionalities with a $C_1-C_{18}$-carboxylic acid obtainable by a process as claimed in claim 13.

15. A process for preparing functionalized cyclopentene-derived oligomer mixtures with hydroxyl functionalities by a single stage functionalization of at least some of the ethylenic double bonds present in an oligomer mixture of the formula I $$R^1R^2C=CH-(CH_2)_3-CH]_nCH^3R^4 \tag{I}$$

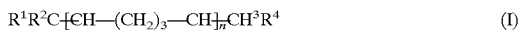

where n is an integer from 1 to 15, and $R^1$, $R^2$, $R^3$ and $R^4$ are, independently of one another, hydrogen or alkyl, wherein the oligomer mixtures of the formula I are obtained by a metathesis reaction of a hydrocarbon mixture comprising acyclic and cyclic olefins, and wherein said hydrocarbon mixture is a $C_5$-hydrocarbon mixture with a total cyclopentene content of at least 5% by weight and a proportion of pentene isomers in the acyclic monoolefins of at least 70% by weight, and wherein the oligomer mixtures of formula I are subjected to a hydroformylation at elevated temperature and under elevated pressure.

16. A process as claimed in claim 15, wherein the reaction is carried out in the presence of a hydroformylation cocatalyst.

17. The process as defined in claim 15, wherein said hydrogenation catalyst is Cu or Ni.

* * * * *